(12) United States Patent
Harner (10) Patent No.: US 9,594,006 B2
(45) Date of Patent: Mar. 14, 2017

(54) PASSIVE DRY DEPOSITION (PAS-DD) COLLECTOR

(71) Applicant: Her Majesty The Queen in Right of Canada, As Represented by the Minister of Environment, Gatineau, Quebec (CA)

(72) Inventor: Tomasz Harner, Toronto (CA)

(73) Assignee: HER MAJESTY THE QUEEN IN RIGHT OF CANADA, AS REPRESENTED BY THE MINISTER OF ENVIRONMENT, Gatineau, Quebec (CA)

(*) Notice: Subject to any disclaimer, the term of this patent is extended or adjusted under 35 U.S.C. 154(b) by 158 days.

(21) Appl. No.: 14/484,059

(22) Filed: Sep. 11, 2014

(65) Prior Publication Data

US 2015/0128732 A1 May 14, 2015

Related U.S. Application Data

(60) Provisional application No. 61/876,522, filed on Sep. 11, 2013.

(51) Int. Cl.
*G01N 1/24* (2006.01)
*G01N 1/22* (2006.01)
(Continued)

(52) U.S. Cl.
CPC ......... *G01N 1/2273* (2013.01); *G01N 1/2205* (2013.01); *G01N 1/2214* (2013.01);
(Continued)

(58) Field of Classification Search
CPC ...................................................... G01N 1/22
(Continued)

(56) References Cited

U.S. PATENT DOCUMENTS 5,308,483 A * 5/1994 Sklar ...................... B01D 29/05
                                                              210/232
5,693,895 A * 12/1997 Baxter ................. G01N 1/2208
                                                              73/28.05

(Continued)

OTHER PUBLICATIONS

Yamasaki, H.; Kuwata, K; Miyamoto, H. Effects of ambient temperature on aspects of airborne polcyclic aromatic hydrocarbons. Environ. Sci. Technol. 1982, 16(4), 189-194.*

(Continued)

*Primary Examiner* — Clayton E LaBalle
*Assistant Examiner* — Kevin Butler
(74) *Attorney, Agent, or Firm* — Jenkins, Wilson, Taylor & Hunt, P.A.

(57) ABSTRACT

A passive dry deposit (Pas-DD) air sampling device and method for sampling volatile, semi-volatile, or particulate matter in air. The Pas-DD device comprises a top cover plate, a bottom plate connected to and spaced a distance apart from the top cover plate, and at least one sampling media supported by the bottom plate and positioned within the device in an orientation accessible for collecting particles in the environment. The top cover plate and bottom plate may be oriented in parallel, and spaced apart a distanced that can be optimized for air sampling a broad size-range of depositing particles. The passive air sampling device and method disclosed are particularly useful for sampling air in regions where access to electricity is difficult, and for estimating atmospheric loadings of polycyclic aromatic hydrocarbons and other semi-volatile compounds.

24 Claims, 6 Drawing Sheets

(51) Int. Cl.
  *G01N 1/20* (2006.01)
  *G01N 1/14* (2006.01)
(52) U.S. Cl.
  CPC .............. *G01N 1/14* (2013.01); *G01N 1/2035* (2013.01); *G01N 1/24* (2013.01); *G01N 2001/2223* (2013.01)
(58) Field of Classification Search
  USPC ...................................................... 73/863.23
  See application file for complete search history.

(56) References Cited

U.S. PATENT DOCUMENTS

| | | | | |
|---|---|---|---|---|
| 6,094,997 | A * | 8/2000 | Lemonnier .......... | G01N 1/2273 73/863.22 |
| 6,514,721 | B2 * | 2/2003 | Spurrell ............... | G01N 1/2205 435/287.5 |
| 6,779,411 | B1 * | 8/2004 | Spurgeon ............. | G01N 1/2205 73/863.23 |
| 7,073,402 | B2 * | 7/2006 | Trakumas ............ | G01N 1/2208 73/863.22 |
| 7,980,147 | B2 | 7/2011 | Tang | |
| 7,998,731 | B2 * | 8/2011 | Daitch ................. | G01N 1/2273 435/287.4 |
| 2008/0233636 | A1 * | 9/2008 | Ryan .................... | G01N 1/2273 435/287.9 |
| 2009/0007699 | A1 * | 1/2009 | Tang .................... | G01N 1/2214 73/863.23 |
| 2009/0301229 | A1 * | 12/2009 | Tang .................... | G01N 1/2214 73/863.23 |
| 2015/0128732 | A1 * | 5/2015 | Harner ................. | G01N 1/2205 73/863.23 |
| 2015/0260617 | A1 * | 9/2015 | Ketcham ............. | G01N 1/2208 73/863.22 |

OTHER PUBLICATIONS

Bargagli, R.; Brown, D. H.; Nelli, L. Metal biomonitoring with mosses: procedures for correcting for soil contamination. Environ. Pollut. 1995, 89(2), 169-175.

Bartkow, M. E.; Kennedy, K. E.; Huckins, J. N.; Holling, N.; Komarova, T.; Müller, J. F. Photodegradation of polyaromatic hydrocarbons in passive air samplers: Field testing different deployment chambers. Environ. Pollut. 2006, 144(2), 371-376.

Bidleman, T. F.; Billings, W. N.; Foreman, W. T. Vapor-particle partitioning of semivolatile organic compounds: estimates from field collections. Environ. Sci. Technol. 1986, 20(10), 1038-1043.

Bozlaker, A.; Muezzinoglu, A.; Odabasi, M. Atmospheric concentrations, dry deposition and air-soil exchange of polycyclic aromatic hydrocarbons (PAHs) in an industrial region in Turkey. J. Hazard. Mater. 2008, 153(3), 1093-1102.

Chaemfa, C.; Wild, E.; Davison, B.; Barber, J. L.; Jones, K. C. A study of aerosol entrapment and the influence of wind speed, chamber design and foam density on polyurethane foam passive air samplers used for persistent organic pollutants. J. Environ. Monit. 2009, 11(6), 1135-1139.

Chang, K. F.; Fang, G. C.; Lu, C.; Bai, H. Estimating PAH dry deposition by measuring gas and particle phase concentrations in ambient air. Aerosol Air Qual. Res. 2003, 3, 41-51.

Davidson, C. I.; Lindberg, S. E.; Schmidt, J. A.; Cartwright, L. G.; Landis, L. R. Dry deposition of sulfate onto surrogate surfaces. J. Geophys. Res., [Atmos.]. 1985, 90(D1), 2123-2130.

Esen, F.; Siddik Cindoruk, S.; & Tasdemir, Y. Bulk deposition of polycyclic aromatic hydrocarbons (PAHs) in an industrial site of Turkey. Environ. Pollut. 2008, 152(2), 461-467.

Galarneau, E.; Bidlman, T. F.; Blanchard, P. Seasonality and interspecies differences in particle/gas partitioning of PAHs observed by the Integrated Atmospheric Deposition Network (IADN). Atmos. Environ. 2006, 40(1), 182-197.

Hageman, K. J.; Hafner, W. D.; Campbell, D. H.; Jaffe, D. A.; Landers, D. H.; Simonich, S. L. M. Variability in pesticide deposition and source contributions to snowpack in western US national parks. Environ. Sci. Technol. 2010, 44(12), 4452-4458.

Halsall, C. J.; Coleman, P. J.; Jones, K. C. Atmospheric deposition of polychlorinated dibenzo-p-dioxins/dibenzofurans (PCDD/Fs) and polycyclic aromatic hydrocarbons (PAHs) in two UK cities. Chemosphere. 2008, 35(9), 1919-1931.

Harner, T.; Su, K.; Genualdi, S.; Karpowicz, J.; Ahrens, L.; Mihele, C.; Schuster, J.; Charland, J.; Narayan, J. Calibration and Application of PUF Disk Passive Air Samplers for Tracking Polycyclic Aromatic Compounds (PAHs). Atmos. Environ. 2013, 75, 123-128.

Holsen, T. M.; Noll, K. E. Dry deposition of atmospheric particles: application of current models to ambient data. Environ. Sci. Technol. 1992, 26(9), 1807-1815.

Jaward, F. M.; Farrar, N. J.; Harner, T.; Sweetman, A. J.; Jones, K. C. Passive air sampling of polycyclic aromatic hydrocarbons and polychlorinated naphthalenes across Europe. Environ. Toxicol. Chem. 2004, 23(6), 1355-1364.

Kelly, E. N.; Short, J. W.; Schindler, D. W.; Hodson, P. V.; Ma, M.; Kwan, A. K.; Fortin, B. L. Oil sands development contributes polycyclic aromatic compounds to the Athabasca River and its tributaries. Proc. Natl. Acad Sci. U.S.A. 2009, 106(52) 22346-22351.

Klánová, J.; Èupr, P.; Kohoutek, J.; Harner, T. Assessing the influence of meteorological parameters on the performance of polyurethane foam-based passive air samplers. Environ. Sci. Technol. 2007, 42(2), 550-555.

Odabasi, M.; Sofuoglu, A.; Vardar, N.; Tasdemir, Y.; Holsen, T. M. Measurement of dry deposition and air-water exchange of polycyclic aromatic hydrocarbons with the water surface sampler. Environ. Sci. Technol. 1999, 33(3), 426-434.

Seaward, M. R. D.; Heslop, J. A.; Green, D.; Bylihska, E. A. Recent levels of radionuclides in lichens from southwest Poland with particular reference to 134Cs and 137Cs. J. Environ. Radioact. 1988, 7(2), 123-129.

Sheu, H. L.; Lee, W. J.; Su, C. C.; Chao, H. R.; Fan, Y. C. Dry deposition of polycyclic aromatic hydrocarbons in ambient air. J. Environ. Eng. (Reston, VA, U.S.). 1996, 122(12), 1101-1109.

Shoeib, M.; Harner, T. Characterization and comparison of three passive air samplers for persistent organic pollutants. Environ. Sci. Technol. 2002, 36(19), 4142-4151.

Simonich, S. L.; & Hites, R. A. Vegetation-atmosphere partitioning of polycyclic aromatic hydrocarbons. Environ. Sci. Technol. 1994, 28(5), 939-943.

Steinnes, E. A critical evaluation of the use of naturally growing moss to monitor the deposition of atmospheric metals. Sci. Total Environ. 1995, 160, 243-249.

Su, Y.; Lei, Y. D.; Wania, F.; Shoeib, M.; Harner, T. Regressing gas/particle partitioning data for polycyclic aromatic hydrocarbons. Environ. Sci. Technol. 2006, 40(11), 3558-3564.

Su, Y.; Wania, F.; Harner, T.; Lei, Y. D. Deposition of polybrominated diphenyl ethers, polychlorinated biphenyls, and polycyclic aromatic hydrocarbons to a boreal deciduous forest. Environ. Sci. Technol. 2007, 41(2), 534-540.

Tasdemir, Y.; Esen, F. Dry deposition fluxes and deposition velocities of PAHs at an urban site in Turkey. Atmos. Environ. 2007, 41(6), 1288-1301.

Thomas, J.; Holsen, T. M.; Dhaniyala, S. Computational fluid dynamic modeling of two passive samplers. Environ. Pollut. 2006, 144(2), 384-392.

Tuduri, L.; Harner, T.; Hung, H. Polyurethane foam (PUF) disks passive air samplers: Wind effect on sampling rates. Environ. Pollut. 2006, 144(2), 377-383.

Wagrowski, D. M.; Hites, R. A. Polycyclic aromatic hydrocarbon accumulation in urban, suburban, and rural vegetation. Environ. Sci. Technol. 1996, 31(1), 279-282.

Wolterbeek, B. Biomonitoring of trace element air pollution: principles, possibilities and perspectives. Environ. Pollut. 2002, 120(1), 11-21.

Yamasaki, H.; Kuwata, K.; Miyamoto, H. Effects of ambient temperature on aspects of airborne polycyclic aromatic hydrocarbons. Environ. Sci. Technol. 1982, 16(4), 189-194.

(56) References Cited

OTHER PUBLICATIONS

Zhang, L.; Gong, S.; Padro, J.; Barrie, L. A size-segregated particle dry deposition scheme for an atmospheric aerosol module. Atmos. Environ. 2001, 35(3), 549-560.

* cited by examiner

Figure 6

PASSIVE DRY DEPOSITION (PAS-DD) COLLECTOR

TECHNICAL FIELD

The present disclosure relates generally to passive air sampling devices and methods for sampling air. More specifically, the present disclosure relates to a passive air sampling device comprising a parallel plate design for use in monitoring volatile, semi-volatile, or particulate matter in air.

BACKGROUND

Devices and methods for monitoring volatile, semi-volatile, or particulate matter in air are highly useful in a wide variety of applications, especially those in which there are public health concerns related to air quality. For example, polycyclic aromatic hydrocarbons (PAHs) are ubiquitous atmospheric pollutants that are a concern due to their toxicity. Investigations of their deposition fluxes are often conducted to assess loadings to terrestrial or aquatic environments that may be at risk. A common approach for estimating deposition of PAHs and other semivolatile air pollutants is based on sampling of ambient air.

Air sampling devices may be categorized as either active or passive air samplers. Active air samplers typically employ pumps to pass air through or over samplers, whereas passive air samplers typically rely on passive processes such as diffusion to sample air.

Three types of passive air samplers are commonly employed. The first, bulk deposition collectors, are continuously open collectors that collect both wet and dry deposition components. Bulk deposition collectors are prone to sampling artifacts (degradation of target analytes exposed to sunlight or revolatilization to air), and are not able to separate dry deposition from wet deposition.

Biomonitoring is a second passive sampling technique that may be employed. In this technique, biomonitors such as pine needles, mosses, and lichens are used to assess deposition. However, this method has associated sources of uncertainty that arise due to inconsistencies with biomonitors as collection substrates. Processes may degrade target analytes following their deposition on biomonitors.

Modeling techniques are a third approach to passive air sampling. Modeling techniques are an indirect approach for assessing deposition using ambient air concentration data and estimated gas- and particle-phase deposition velocities to calculate deposition fluxes. This approach requires information on wind speed, topography, particle-size distribution, and chemical particle-gas partitioning data in order to provide an estimate for deposition flux. This is a data-heavy approach that could result in high uncertainty depending on the availability of data.

One example of a commercially available passive air sampler is the TE-200 PUF passive air sampler (Tisch Environmental, herein referred to by the acronym PAS). The PAS device is a passive air sampler employing a polyurethane foam (PUF) collection media. The PAS device comprises upper and lower fitted bowls joined by a hinge on one side. An assembled PAS device adopts a double dome shape. The upper and lower fitted bowls assemble such that a gap is formed between the rims of the open ends of the two bowls. A PUF collection media is supported within the chamber formed by the fitted bowls. Air circulation may enter and exit the chamber, allowing for passive sampling of the air through exposure to the contained PUF disk.

While the PAS device is useful for a variety of passive air sampling applications, the double-dome chamber design of the PAS device inherently precludes larger depositing particles. In many applications, for example, in the case of polyaromatic hydrocarbon (PAH) sampling, larger particles dominate the dry deposition particle component and thus a passive air sampling device operating in the full size-range of depositing particles would be more desirable.

A variety of other passive air sampling devices are also known, for example, as described and taught in U.S. Pat. No. 7,980,147B2 to Tang.

SUMMARY

It is an object of the disclosure to provide a passive air sampling device which is useful for sampling broader ranges of particle sizes in the environment.

According to an aspect of the present disclosure, there is provided a passive air sampling device comprising:
  a top cover plate;
  a bottom plate connected to and spaced a distance apart from the top cover plate; and
  at least one sampling media supported by the bottom plate and positioned within the device in an orientation accessible for collecting particles in the environment.

In an embodiment of the passive air sampling device, the top cover plate and the bottom plate may be connected by one or more vertical spacers. In further embodiments, which are non-limiting, the vertical spacers may be height adjustable to facilitate adjustment of the distance between the top cover plate, the sampling media and/or the bottom plate.

In further non-limiting embodiments of the passive air sampling device, the bottom plate may comprise at least one perforation or opening to increase accessibility of the sampling media to particles in the environment.

The device may also further comprise a support ring, which can be connected to and positioned between the top cover plate and the bottom plate. Without wishing to be limiting, the support ring may in further embodiments be substantially parallel to the top cover plate and the bottom plate, and provide additional support to the sampling media. In yet further embodiments, the sampling media may be supported between the bottom plate and the support ring.

It is also envisioned that the device may, in further non-limiting embodiments, comprise a bracket for mounting the device to a support structure.

The sampling media may, in non-limiting embodiments of the described device, be spaced apart from the top cover plate a distance, for example, ranging from about 0.1 cm to about 7 cm, or from about 1 cm to about 3 cm, or at a distance of approximately 2 cm, including distances within these ranges such as 1, 2, 3, 4, 5, 6 and 7 cm.

In additional embodiments of the device, which are not limiting, the sampling media may be any of a range of known media suitable for sampling of volatile, semi-volatile, or particulate matter in air. For example, the sampling media may comprise a porous sampling media, or in particular embodiments the media may be a polyurethane foam (PUF), glass fiber filter and/or other polymer matrices.

Other embodiments of the device may include one or more of the top cover plate, support ring, sampling media, and bottom plate shaped to allow for multidirectional air sampling, e.g. rounded or circular in shape. In addition, the bottom plate may comprises a beveled edge in further embodiments of the device, in order to optimize air flow characteristics.

In addition, in further non-limiting embodiments, the top cover plate may be dimensioned with a larger diameter than the sampling media, and be effective to cover the sampling media while maintaining accessibility of the sampling media for collecting particles in the environment. In certain embodiments, it may also be desirable for the diameter of the top cover plate to be larger than the diameter of the support ring, the sampling media, and the bottom plate.

Further embodiments may include devices adapted for monitoring air deposition of volatile, semi-volatile, or particulate matter in a region, or for monitoring organic or inorganic air toxins or contaminants, and particularly for monitoring air deposition of polycyclic aromatic hydrocarbons.

According to a further aspect of the present disclosure, there is also provided a method of sampling air for volatile, semi-volatile, or particulate matter in a region. The method comprises:
  positioning at least one passive air sampling device as described in any of the paragraphs above in a sampling region and allowing any volatile, semi-volatile, or particulate matter in the air to deposit on the sampling media over a period of time; and
  collecting the sampling media from the at least one passive air sampling device at the end of the air sampling period.

In addition, the above method may also comprise additional steps of analyzing the sampling media collected from the passive air sampling device(s), and determining concentrations of volatile, semi-volatile, and/or particulate matter in the sampled air based on quantities of volatile, semi-volatile, or particulate matter deposited on the sampling media.

BRIEF DESCRIPTION OF THE DRAWINGS

These and other features of the disclosure will become more apparent from the following description in which reference is made to the appended drawings, wherein.

DETAILED DESCRIPTION

The present disclosure generally relates to a passive air sampling device and method for sampling air.

In particular embodiments, the passive air sampling device comprises a parallel plate-type design that is useful for monitoring volatile, semi-volatile, or particulate matter in air. Without wishing to be limiting in any way, it is envisioned that certain preferred embodiments of the passive air sampling device may be easily deployed, affordable to manufacture, and/or provide an accurate, reliable, and consistent sampling of air contaminants of interest in a region without need for electricity or other power source.

The open design of the passive air sampling device described herein can also, in further preferred yet non-limiting embodiments, allow for better measurements of the downward flux of PAHs (i.e. dry particle deposition) due to the ability of the device to collect a broader size range of depositing particles as compared to other known devices.

Figure 1:
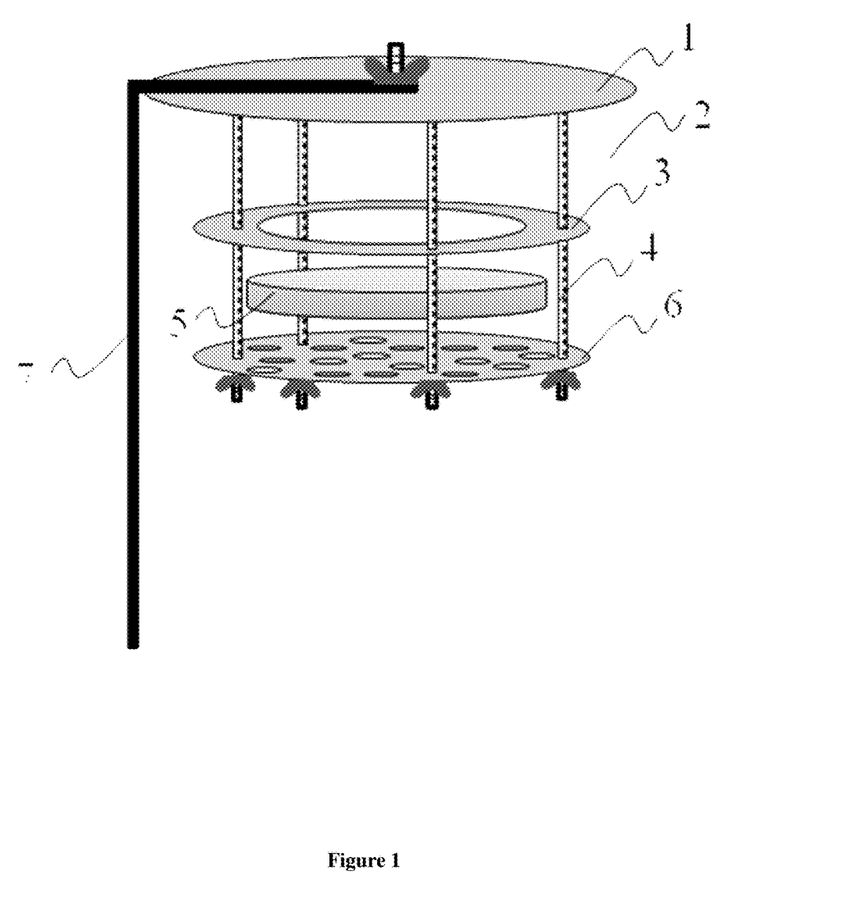
FIG. 1 shows a schematic view of a passive dry deposit air sampler in accordance with one example of an embodiment of the disclosure.

The passive air sampling device of the present disclosure is described in further detail below with reference to the passive dry deposit collector (Pas-DD) illustrated in FIG. 1.

As illustrated, the Pas-DD device comprises a top cover plate (1), a perforated bottom plate (6), and one or more sampling media (5) supported by the bottom plate (6). The top cover plate (1) and bottom plate (6) are oriented in parallel, forming an open gap (2). The flat plate design illustrated may be used in certain embodiments of the device to promote unobstructed flow of air between the plates, and with minimal turbulence. As illustrated, the top cover plate (1) may also have a larger diameter than the bottom plate (6), the one or more sampling media (5), and the support ring (3), such that the top cover plate (1) can shield the sampling media (5) from wet deposition and direct sunlight which can enhance degradation of some target analytes. The device as illustrated also includes vertical spacers (4) which span the open gap (2) formed between the top cover plate (1) and the bottom plate (6). The vertical spacers (4) may be height adjustable to allow for adjustment of the open gap (2) distance. A support ring (3) is also provided, parallel to and between the top cover plate (1) and the bottom plate (6). The support ring (3) is positioned above the sampling media (5) and provides additional support to the sampling media (5). A mounting bracket is also secured to the device, affixed to the top surface of the cover plate (1) in the illustrated embodiment, in order to facilitate mounting of the Pas-DD device in an area to be sampled.

The sampling media (5) of the Pas-DD device may be of a range of media types suitable for the sampling of volatile, semi-volatile, or particulate matter in air. For example, the sampling media (5) may be a stacked glass fiber filter, or a porous sampling media such as polyurethane foam (PUF). The sampling media (5) may also comprise a plurality of sampling media, in order to facilitate sampling of a plurality of different analytes.

As illustrated, the top cover plate (1), the support ring (3), the sampling media (4), and the bottom plate (6) are circular in shape. This particular shape can be preferred in some embodiments, as circular shapes tend to facilitate multidirectional air sampling. In addition, the bottom plate (6) may feature a beveled edge, which can also improve air flow characteristics.

The Pas-DD device is useful for monitoring air deposition of volatile, semi-volatile, or particulate matter in air. Accordingly, the device can be used for monitoring organic or inorganic air toxins or contaminants. The device is particularly useful for monitoring polycyclic aromatic hydrocarbons (PAHs), for example in the oil sands region or other urban or industrial areas to assess regional deposition of PAHs and other chemicals.

The Pas-DD device can also be employed in an air sampling method of the present disclosure. For example, the method will typically include: deploying at least one Pas-DD device in a region to be studied; allowing air sampling to occur over a duration of time and collecting the Pas-DD devices (or at least the sampling media thereof) at the end of the sampling duration. In addition, the methodology may also include the analytical steps of analyzing the sampling media from the Pas-DD devices and determining the concentration(s) of the target analytes using any of a variety of known techniques.

Further embodiments and details of the disclosure will become apparent based on the following examples.

EXAMPLES

The passive dry deposition (Pas-DD) collector was used for estimating atmospheric loadings (dry deposition fluxes or maps) for polycyclic aromatic hydrocarbons (PAHs) and other semi-volatile compounds. This time-integrated sampler is particularly well suited for deployment in remote sites over large regions, where sampling using conventional air sampling equipment is logistically challenging due to the nature of the environment and lack of access to electricity and infrastructure. Pas-DD collectors based on a parallel plate design were co-deployed with conventional polyurethane foam (PUF) disks passive air samplers (PAS) in outdoor urban air over different seasons. Two configurations of sampling media (PUF only vs. stacked glass fiber filter (GFF) on PUF) were used. For both samplers, higher accumulation of PAHs was observed when only the PUF disk was used as the sampling medium. The Pas-DD and the PAS accumulated gas-phase PAHs (dry gaseous deposition component) to a similar extent. For the higher molecular weight PAHs that are associated with particles, the Pas-DD was enriched relative to the PAS. Dry deposition velocities derived from the Pas-DD were approximately 0.16 cm/s for gas-phase PAHs and up to 0.8 cm/s for particle-phase PAHs.

Field deployments of the Pas-DD collector were performed during a summer and winter season and alongside conventional PUF disk PAS like those currently used in the oil sands air monitoring program (Harner et al., 2013). Two configurations of collection media were also tested for their ability to capture dry gas- and particle-phase deposition of PAHs.

Testing was performed on the Pas-DD to evaluate the effect of the gap-opening between plates (from 2 cm to 7 cm) on the number of particles that were deposited onto a glass fiber filter situated on top of the PUF disk. Field tests were carried out during 2011 to evaluate the effect of gap opening on the particle collection efficiency of the Pas-DD. This was done for variable gap sizes between the top two plates (i.e. cover plate and support ring) ranging from 7 cm down to 2 cm. The sampling substrate was a glass fiber filter (Whatman 1824-042) positioned on top of a PUF disk (Tisch Scientific TE-1014, 14 cm diameter×1.35 cm thick). Interpretation of particle sampling was based on visual inspection of the PUF disks using optical microscopy using an Olympus BX51 fitted with a MPLNSxBD lens. This was facilitated by a particle counting software (Lumenera Corporation Infinity Analyze v6.0) that averaged results from several representative regions on the GFF.

The results showed that for larger openings down to about 7 cm, the GFF was exposed to the elements (sun, wind and even precipitation) and resulted in physical damage to GFF. This resulted in reduced particle sampling presumably due to particle loss as a result of wind abrasion. With smaller gap openings (less than 4 cm) the GFF was better protected from the elements. Particle counts on the GFF for gap openings ranging from 4 cm and 2 cm were not significantly different ($p<0.05$).

Based on these findings, the revised Pas-DD design was based on the smaller gap opening of 2 cm to optimize conditions for protecting the sampling substrate from meteorological effects while not impacting the ability of particles to deposit onto the sampling surface. It was shown that even for gaps as small as 2 cm, the full size-range of particles were able to deposit onto the sampling medium (i.e. the larger particles were not excluded). For field testing of the Pas-DD in the current study, the 2 cm gap configuration was used as this provided optimal protection for the PUF disk from wet deposition and sunlight.

Methods:

Sampler Deployment

Figure 5:
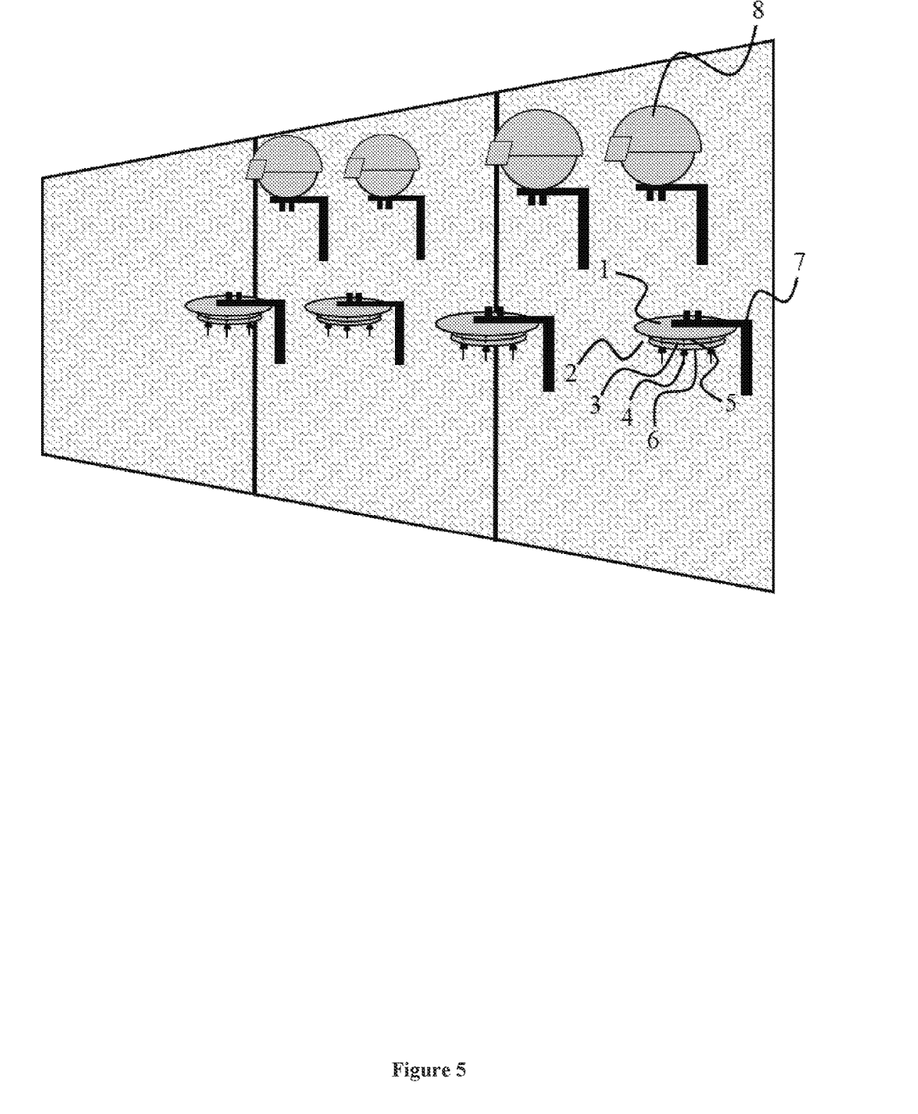
FIG. 5 shows an example of a deployment setup of PAS and Pas-DD collectors on the top and bottom, respectively. Pas-DD collectors are deployed in accordance with an embodiment of the present disclosure.

Samplers were deployed during two sampling campaigns at the Environment Canada (Downsview) field station in Toronto, Ontario (long/lat: 43.780611, −79.467953). This is a background urban site that receives PAHs from a wide range of typical urban sources (e.g. vehicle traffic, residential and recreational emissions, and light industry). The first campaign took place during the summer (June-August, 2012, lasting 63 days) and the second campaign during the winter (November 2012-January 2013, lasting 61 days). During each campaign, a total of 8 samplers were deployed side-by-side: 4 Pas-DD collectors (FIG. 1) and 4 conventional PUF disk PAS (FIG. 5). The samplers were mounted approximately 1.5 to 2 m above the ground (see FIG. 5).

Two configurations of the sampling media were tested in duplicate for both the Pas-DD and PAS. Configuration #1 used the PUF disk alone as the collecting medium (Tisch Scientific TE-1014, 14 cm diameter×1.35 cm thick); whereas in Configuration #2, a Whatman 1824-042 glass micro-fibre filter (GFF) was placed on top of the PUF disk (i.e. GFF-PUF). This was repeated in both campaigns and field blanks were collected for PUF disks (n=3) and GFF (n=2).

TABLE 1

Weights (g) of glass fibre filter (GFF) and PUF disks as a whole and the portion removed for optical microscopy analysis from field blanks (FB), summer campaign (S) and winter campaign (W).

|  | Whole | Portion removed | % of section removed |
| --- | --- | --- | --- |
| (FB)-GFF-01 | 1.2494 | 0.1473 | 11.79% |
| (FB)-GFF-02 | 1.2466 | 0.1599 | 12.83% |
| (FB)-PUF-01 | 4.5455 | 0.4175 | 9.18% |
| (FB)-PUF-02 | n/a | n/a | Whole PUF used |
| (FB)-PUF-03 | n/a | n/a | Whole PUF used |
| (FB)-PUF-04 | n/a | n/a | Whole PUF used |

TABLE 1-continued

Weights (g) of glass fibre filter (GFF) and PUF disks as a whole
and the portion removed for optical microscopy analysis from field
blanks (FB), summer campaign (S) and winter campaign (W).

|  | Pas-DD | | | PAS | | |
| --- | --- | --- | --- | --- | --- | --- |
|  | Whole | Portion removed | % of section removed | Whole | Portion removed | % of section removed |
| (S)-GFF-01 | 1.8650 | 0.2692 | 14.43% | 1.2538 | 0.1628 | 12.98% |
| (S)-GFF-02 | 3.4883 | 0.6911 | 19.81% | 1.2738 | 0.1703 | 13.37% |
| (S)-PUF-01 | 3.7757 | 0.5707 | 15.12% | 4.7544 | 0.6807 | 14.32% |
| (S)-PUF-02 | 4.8275 | 0.8282 | 17.16% | 4.1427 | 0.582 | 14.05% |
| (S)-PUF-03 | 4.8812 | 0.7302 | 14.96% | 5.0909 | 0.7332 | 14.40% |
| (S)-PUF-04 | 4.0158 | 0.5649 | 14.07% | 4.6335 | 0.6943 | 14.98% |
| (W)-GFF-01 | 1.25299 | 0.16913 | 13.50% | 1.25615 | 0.1644 | 13.09% |
| (W)-GFF-02 | 1.25971 | 0.15599 | 12.38% | — | — | — |
| (W)-PUF-01 | 4.30005 | 0.50989 | 11.86% | 4.57016 | 0.62589 | 13.70% |
| (W)-PUF-02 | 4.61315 | 0.64016 | 13.88% | 4.102 | 0.56368 | 13.74% |
| (W)-PUF-03 | 4.26863 | 0.58701 | 13.75% | 4.58907 | 0.52175 | 11.37% |
| (W)-PUF-04 | 4.6667 | 0.73229 | 15.69% | 4.43081 | 0.56767 | 12.81% |

Analysis Using Optical Microscopy

At the end of each deployment period, a ~15% portion of each collected GFF and PUF disk were cut out and removed for visual analysis by optical microscopy using an Olympus BX51 fitted with a MPLN5xBD lens. The percentage of the portion removed was calculated based on weight by difference (Table 1).

Optical microscopy is sensitive enough to provide a visual assessment of particles as small as ~1 μm that have deposited onto the GFF and PUF disk surfaces. In the context of assessing depositing particles, the dominant contribution comes from particles that are larger than 1 μm and that are easily visible by this technique (Holsen et al., 1992).

GFF and PUF Sample Extraction, Analysis, and QA/QC

The remaining portion (~85%) of the GFFs and PUF disks were analyzed according to the methods used in Harner et al., 2013 and results were scaled-up accordingly to represent 100% of the sample. Field blank results were used to calculate corresponding limit of detection (LOD) values as (mean field blank value+3*STDEV). When PAH target analytes were not detected in the field blanks or samples, ⅔ of the instrument detection limit (IDL) value for the corresponding analyte was substituted. The IDL was calculated by extrapolating the lowest calibration standard to a concentration that would result in a signal to noise ratio of 3:1, assuming linear response. Field blank, LOD, and IDL values are summarized in Table 2 and Table 3.

TABLE 2

Results (ng PUF-1) for PUF field blanks, instrument detection limits (IDL),
field blank mean (FMB), and limit of detection limits (LOD = FMB +
3STDEV) for target analytes. Values have been weight corrected using Table 1.

|  | FB-PUF-01 | FB-PUF-02 | FB-PUF-03 | FB-PUF-04 | IDL | FBM | 3STDEV | LOD |
| --- | --- | --- | --- | --- | --- | --- | --- | --- |
| Naphthalene | 14.9802 | 10.18 | 18.29 | 13.21 | 0.078273 | 14.17 | 10.17 | 24.33 |
| Acenaphthylene | 34.1967 | 31.73 | 31.35 | 31.34 | 0.364188 | 32.15 | 4.12 | 36.28 |
| Acenaphthene | 16.0611 | 15.36 | 14.84 | 14.24 | 0.527009 | 15.13 | 2.32 | 17.45 |
| Fluorene | 25.9096 | 25.06 | 23.95 | 26.52 | 0.174393 | 25.36 | 3.34 | 28.7 |
| Phenanthrene | 4.9461 | 3.49 | 6.69 | 5.36 | 0.220467 | 5.12 | 3.95 | 9.07 |
| Anthracene | 1.9802 | 1.9802 | 1.9802 | 1.9802 | 2.970297 | 1.98 | 0 | 1.98 |
| Retene | 2.0408 | 2.0408 | 2.0408 | 2.0408 | 3.061224 | 2.04 | 0 | 2.04 |
| Fluoranthene | 1.4631 | 2.53 | 1.7 | 0.53 | 0.079856 | 1.56 | 2.47 | 4.02 |
| Pyrene | 0.9608 | 1.42 | 1.06 | 0.47 | 0.150451 | 0.98 | 1.18 | 2.15 |
| Dibenzothiophene | 0.7097 | 0.92 | 0.0316 | 0.69 | 0.04747 | 0.59 | 1.16 | 1.74 |
| Benzo(a)anthracene | 1.1574 | 0.65 | 0.76 | 0.0899 | 0.134922 | 0.66 | 1.32 | 1.99 |
| Chrysene | 0.0706 | 0.0706 | 0.19 | 0.0706 | 0.105951 | 0.1 | 0.18 | 0.28 |
| Benzo(b)fluoranthene | 0.131 | 0.25 | 0.41 | 0.085 | 0.127483 | 0.22 | 0.44 | 0.65 |
| Benzo(k)fluoranthene | 0.085 | 0.085 | 0.15 | 0.085 | 0.127483 | 0.1 | 0.1 | 0.2 |
| Benzo(a)pyrene | 0.3386 | 0.3386 | 1.59 | 0.3386 | 0.507829 | 0.65 | 1.88 | 2.53 |
| Perylene | 0.3386 | 0.3386 | 0.3386 | 0.3386 | 0.507829 | 0.34 | 0 | 0.34 |
| Indeno(123-cd)pyrene | 1.5504 | 0.69 | 0.0597 | 0.0597 | 0.089499 | 0.59 | 2.12 | 2.71 |
| Dibenz(ah)anthracene | 1.4522 | 0.0518 | 0.0518 | 1.62 | 0.077755 | 0.79 | 2.58 | 3.37 |
| Benzo(ghi)perylene | 0.2293 | 0.74 | 0.24 | 0.0746 | 0.111878 | 0.32 | 0.87 | 1.19 |

Note:

values flagged in red indicate that ⅔ of the IDL value was substituted when no peak was detected in the blanks.

TABLE 3

Results (ng GFF-1) for GFF field blanks, instrument detection limits (IDL), field blank mean (FMB), and limit of detection limits (LOD = FMB + 3STDEV) for target analytes. Values have been weight corrected using Table 1.

|  | FB-GFF-01 | FB-GFF-02 | IDL | FBM | 3STDEV | LOD |
|---|---|---|---|---|---|---|
| Naphthalene | 12.3192 | 10.8652 | 0.08 | 11.59222 | 3.08 | 14.68 |
| Acenaphthylene | 0.2428 | 0.2428 | 0.36 | 0.242792 | 0 | 0.24 |
| Acenaphthene | 16.5113 | 17.0369 | 0.53 | 16.7741 | 1.11 | 17.89 |
| Fluorene | 26.7401 | 26.0179 | 0.17 | 26.37898 | 1.53 | 27.91 |
| Phenanthrene | 5.4442 | 4.829 | 0.22 | 5.136574 | 1.3 | 6.44 |
| Anthracene | 1.9802 | 1.9802 | 2.97 | 1.980198 | 0 | 1.98 |
| Retene | 2.0408 | 2.0408 | 3.06 | 2.040816 | 0 | 2.04 |
| Fluoranthene | 5.7907 | 4.8403 | 0.08 | 5.315489 | 2.02 | 7.33 |
| Pyrene | 5.6901 | 4.6485 | 0.15 | 5.169281 | 2.21 | 7.38 |
| Dibenzothiophene | 0.436 | 0.44 | 0.05 | 0.438002 | 0.01 | 0.45 |
| Benzo(a)anthracene | 1.6433 | 0.9252 | 0.13 | 1.284244 | 1.52 | 2.81 |
| Chrysene | 3.5549 | 2.8771 | 0.11 | 3.215998 | 1.44 | 4.65 |
| Benzo(b)fluoranthene | 6.3385 | 5.3367 | 0.13 | 5.837593 | 2.13 | 7.96 |
| Benzo(k)fluoranthene | 2.5153 | 2.1663 | 0.13 | 2.340772 | 0.74 | 3.08 |
| Benzo(a)pyrene | 3.4096 | 3.0012 | 0.51 | 3.20539 | 0.87 | 4.07 |
| Perylene | 0.9167 | 0.6093 | 0.51 | 0.76297 | 0.65 | 1.42 |
| Indeno(123-cd)pyrene | 4.8852 | 3.9151 | 0.09 | 4.400151 | 2.06 | 6.46 |
| Dibenz(ah)anthracene | 1.1179 | 0.3159 | 0.08 | 0.716906 | 1.7 | 2.42 |
| Benzo(ghi)perylene | 4.1474 | 3.4412 | 0.11 | 3.794308 | 1.5 | 5.29 |

Note:
values flagged in red indicate that ⅔ of the IDL value was substituted when no peak was detected in the blanks.

Results and Discussion:
Optical Microscopy

Figure 2:
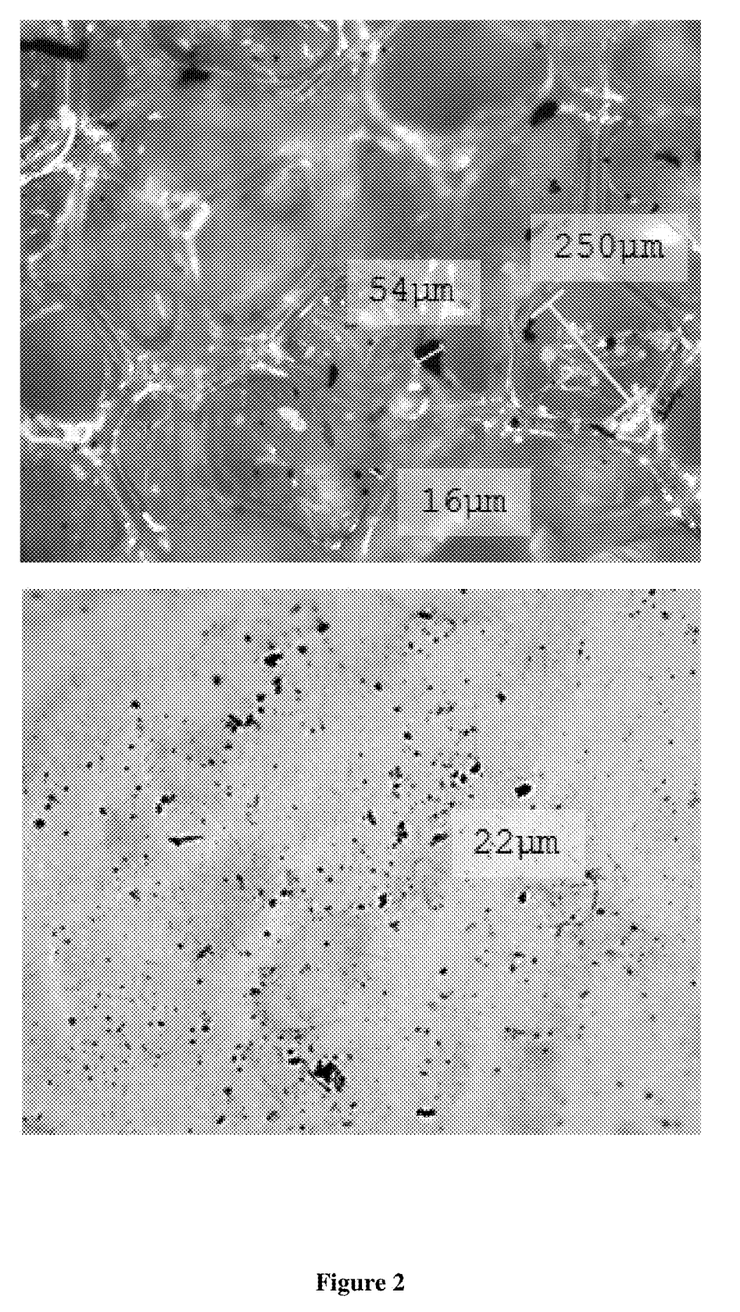
FIG. 2 shows optical microscopy images of a polyurethane foam (PUF)disk (top) and glass fiber filter (GFF) (bottom) collected from a passive dry deposit air sampling device during a winter campaign. The images are at 50× magnification.

FIG. 2 is a 50× magnification of a portion of PUF disk and GFF following the winter deployment in the Pas-DD under the PUF only and GFF-PUF configurations, respectively. Many of the collected particles have passed through the pores (~200-250 μm in diameter) on the exterior surface of the PUF disk and have become entrained in the matrix, with little chance for resuspension or chemical desorption. In contrast, particles collected on the GFF are positioned on the surface of the more densely woven GFF matrix, where pore sizes are less than about 0.1 μm. These particles are more exposed to air with the potential for revolatilization of bound chemical. Inspection of the underside of the PUF and GFF samples by optical microscopy revealed very few particles, indicating that particle collection was predominantly to the top surfaces of the sampling substrates.

PAH Analysis

Figure 3:
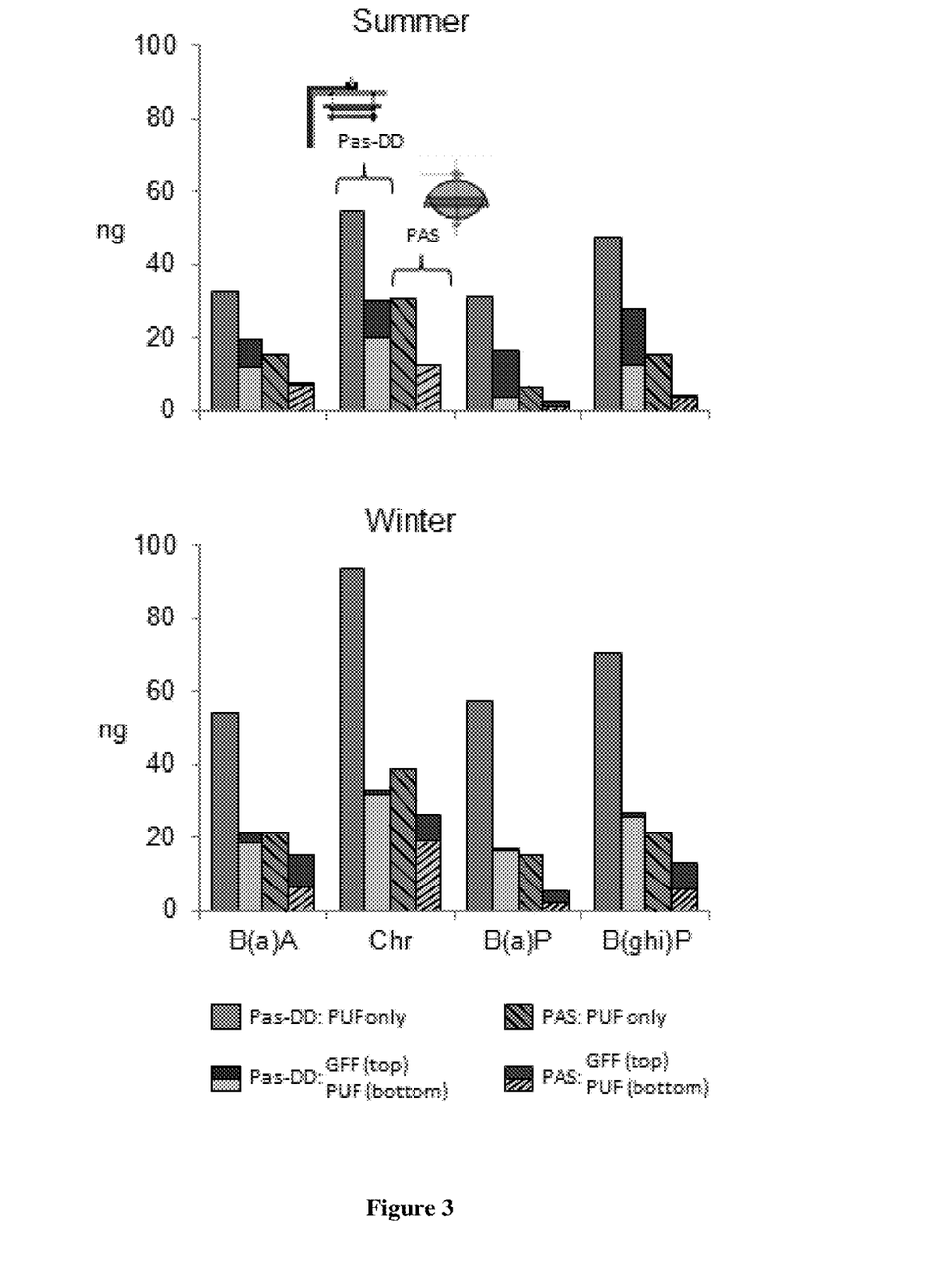
FIG. 3 shows the measured concentrations of representative particle-phase polycyclic aromatic hydrocarbons (PAHs) measured by the passive air sampler (PAS) and the passive dry deposit air sampler (Pas-DD) illustrated in FIG. 1, during summer and winter campaigns. As indicated, both polyurethane foam and stacked glass fiber filter collection media were employed in the PAS and Pas-DD samplers.
Figure 6:
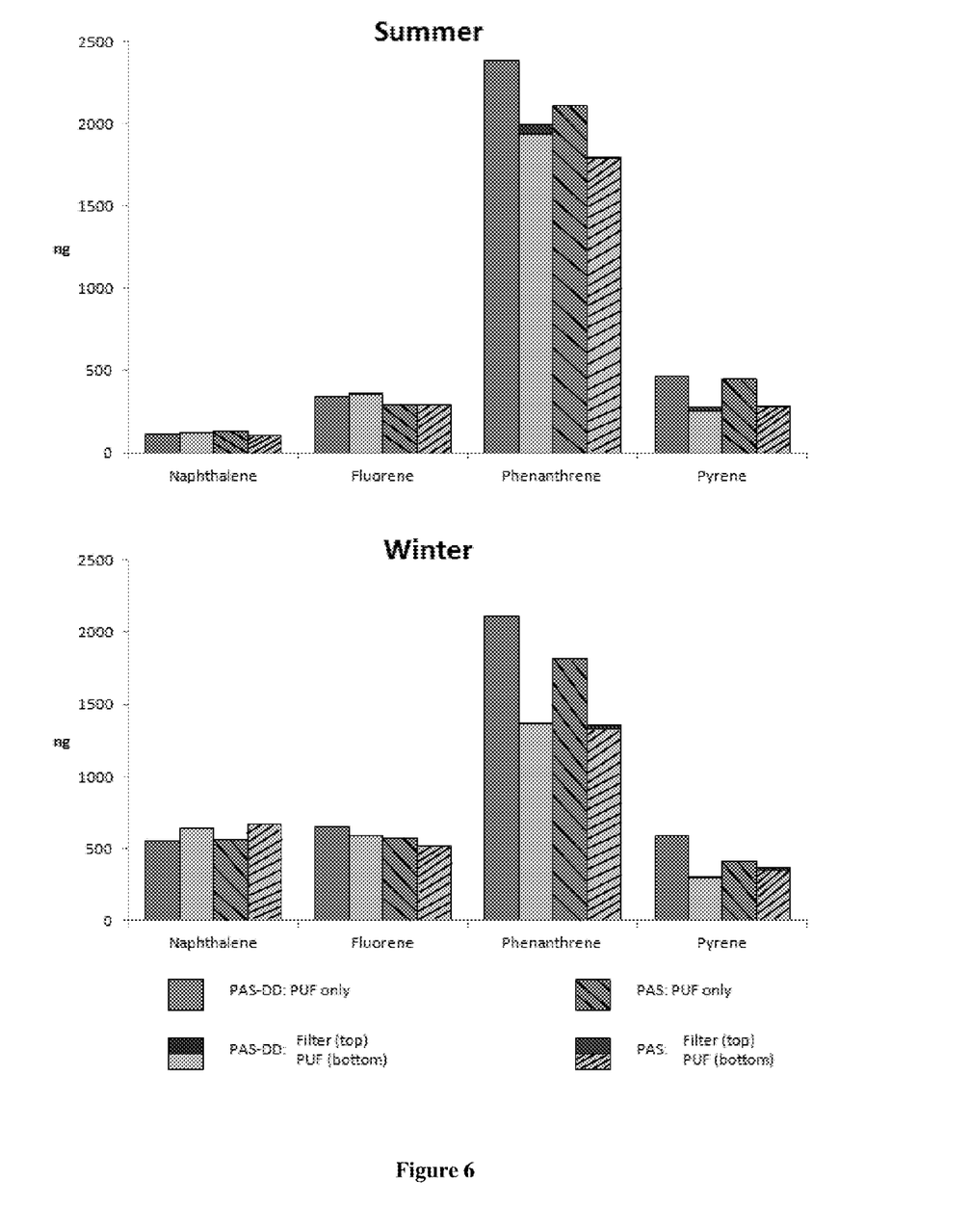
FIG. 6 shows the measured concentrations of representative gas-phase PAHs measured by the PAS and the Pas-DD sampler during summer and winter campaigns. As indicated, both PUF and stacked glass fiber filter collection media were employed in the PAS and Pas-DD samplers.

Final compound concentrations (ng per PUF and ng per GFF) are presented in Table 4 with results for selected PAHs illustrated in FIG. 2 (for representative particle-associated PAHs) and FIG. 6 (for representative gas phase PAHs). Of the four configurations tested (Pas-DD$_{(PUF\ only)}$, Pas-DD$_{(GFF-PUF)}$, PAS$_{(PUF\ only)}$, PAS$_{(GFF-PUF)}$), highest amounts of PAHs were collected on the Pas-DD that used only a PUF disk as the collection substrate (FIG. 3). This was even more apparent for the winter period when the partitioning of PAHs shifts to the particle-phase due to reduced volatility at colder temperatures (Bidleman et al., 1986; Yamasaki et al., 1982). The double-domed PAS also showed greater accumulation of PAHs for the PUF only configuration compared to the GFF-PUF arrangement.

TABLE 4

Air concentration (ng GFF1 and ng PUF-1) of target analytes during the summer and winter deployment for the passive air sampler dry deposition (PAS-DD) and the passive air sampler (PAS). Values have been weight corrected using Table S1 and represent concentrations as ng per whole GFF and ng per whole PUF.

|  | Summer | | | |
|---|---|---|---|---|
|  | PAS-DD | | PAS | |
|  | GFF-PUF | PUF | GFF-PUF | PUF |
| Naphthalene | 0 | 121.07 | 116.56 | 0 | 108 | 130.29 |
| Acenaphthylene | 46.73 | 13.16 | 19.44 | 37.38 | 12.54 | 17.43 |
| Acenaphthene | 0.54 | 139.18 | 153.37 | 0 | 138.89 | 154.45 |
| Fluorene | 2.11 | 356.21 | 340.21 | 0 | 289.75 | 372.4 |
| Phenanthrene | 50.27 | 1939.24 | 2381 | 6.42 | 1789.54 | 2110.07 |
| Anthracene | 2.71 | 0.99 | 0 | 0 | 0 | 0 |
| Retene | 0.88 | 82.7 | 128.03 | 0 | 102.36 | 137.79 |
| Fluoranthene | 27.53 | 735.56 | 1169.36 | 6.87 | 671.56 | 961.14 |
| Pyrene | 23.87 | 253.51 | 466.8 | 5.2 | 280.13 | 449.89 |
| Dibenzothiophene | 0.6 | 99.31 | 109.35 | 0.32 | 79.48 | 105.73 |
| Benzo(a)anthracene | 7.63 | 11.68 | 32.87 | 0.18 | 6.63 | 15.14 |
| Chrysene | 9.7 | 19.98 | 54.4 | 0 | 12.43 | 30.2 |
| Benzo(b)fluoranthene | 20.72 | 22.02 | 91.21 | 4.37 | 37.41 | 27.98 |
| Benzo(k)fluoranthene | 7.16 | 7.38 | 26.45 | 1.78 | 8.02 | 8.93 |
| Benzo(a)pyrene | 13.01 | 3.38 | 30.87 | 2.09 | 0.63 | 6.44 |

TABLE 4-continued

Air concentration (ng GFF1 and ng PUF-1) of target analytes during the summer and winter deployment for the passive air sampler dry deposition (PAS-DD) and the passive air sampler (PAS). Values have been weight corrected using Table S1 and represent concentrations as ng per whole GFF and ng per whole PUF.

| | | | | | | |
|---|---|---|---|---|---|---|
| Perylene | 1.44 | 1.95 | 6.17 | 0.29 | 0.59 | 1.95 |
| Indeno(123-cd)pyrene | 6.52 | 5.15 | 27.12 | 0 | 4.82 | 10.9 |
| Dibenz(ah)anthracene | 0.86 | 0.03 | 4.98 | 0 | 0.7 | 0.59 |
| Benzo(ghi)perylene | 15.67 | 12.23 | 47.63 | 0.59 | 3.51 | 15.05 |

| | Winter | | | |
|---|---|---|---|---|
| | PasAS-DD | | PAS | |
| | GFF-PUF | PUF | GFF-PUF | PUF |
| Naphthalene | 0 | 639.48 | 554.16 | 0 | 666.39 | 561.73 |
| Acenaphthylene | 30.4 | 20.04 | 34.97 | 29.93 | 9.79 | 11.14 |
| Acenaphthene | 0 | 174.61 | 176.31 | 0 | 181.27 | 182.88 |
| Fluorene | 0 | 591.02 | 656.5 | 0 | 518.08 | 573.03 |
| Phenanthrene | 9.03 | 1360.09 | 2104.39 | 20.87 | 1328.8 | 1814.76 |
| Anthracene | 0 | 2.09 | 10.77 | 0 | 2.29 | 6.68 |
| Retene | | | | | 0 | 0 |
| Fluoranthene | 11.6 | 375.86 | 650.66 | 21.59 | 449.02 | 483.75 |
| Pyrene | 7.24 | 299.03 | 587.51 | 18.26 | 350.43 | 408.91 |
| Dibenzothiophene | 0.1 | 46.4 | 75.19 | 0.66 | 41.58 | 87.15 |
| Benzo(a)anthracene | 2.6 | 18.41 | 54.29 | 8.81 | 16.9 | 21.23 |
| Chrysene | 0.86 | 31.8 | 93.71 | 7.32 | 18.99 | 38.87 |
| Benzo(b)fluoranthene | 1.75 | 41.03 | 122 | 6.67 | 11.87 | 40.84 |
| Benzo(k)fluoranthene | 0.36 | 14.47 | 41.84 | 2.97 | 4.33 | 12.89 |
| Benzo(a)pyrene | 0.5 | 16.45 | 57.38 | 3.5 | 1.85 | 15.02 |
| Perylene | 0 | 3.59 | 12.59 | 0.21 | 0.5 | 3.2 |
| Indeno(123-cd)pyrene | 0 | 18.18 | 51.57 | 0.18 | 2.13 | 14.47 |
| Dibenz(ah)anthracene | 0 | 2.72 | 12.42 | 0 | 0 | 3.73 |
| Benzo(ghi)perylene | 1.25 | 25.27 | 70.52 | 6.84 | 6.02 | 21.39 |

The greater sampling of PAHs by the PUF-only configuration versus the GFF-PUF configuration may be attributed to the porosity of the PUF that allows depositing particles to become entrained (see FIG. 2), thereby reducing the chances of re-suspension or rebounding (i.e. particles blowing off the substrate). This entrainment of particles into the PUF matrix has been previously reported (Chaemfa et al., 2009). Loss of chemical from these particles by revolatilization is also less likely as the PUF disk itself has a high sorptive capacity and is likely to scavenge PAHs that are bound to or released from the particles. Particle rebounding and revolatilization of chemical is more likely to occur for the GFF where deposited particles are associated with the surface of the GFF (that has limited sorptive capacity for PAHs) and are more vulnerable to episodic wind gusts (ref).

The higher accumulation of PAHs by the Pas-DD compared to the conventional PAS (for both the PUF only and GFF-PUF configurations) is attributed by the double-dome chamber used for the PAS which filters out the larger depositing particles (Klanova et al., 2008; Chaemfa et al., 2009; Jaward et al., 2004). Dry deposition of PAHs is a combination of dry gaseous deposition+dry particle deposition. In essence, the two sampler configurations should be sampling gas-phase PAHs at similar rates (i.e. dry gaseous deposition has no downward bias as it is a function of diffusivity in air). Slightly lower total accumulation of the gas-phase component might be expected in the Pas-DD compared to the PAS chamber (when results are expressed as ng/sample) due to the positioning of the PUF in the Pas-DD. Approximately 36% of the PUF total outer surface area is covered by the support ring and perforated plate that holds the PUF disk in place; but countering reduction in sampling for the Pas-DD is the higher wind speed through the Pas-DD plates that will reduce air-side mass transfer resistance and enhance chemical sampling rates (Shoeib et al., 2002; Thomas et al., 2006; Tuduri et al., 2006). Because of its open design, the Pas-DD provides a better measure of the downward flux of PAHs (i.e. dry particle deposition) as the Pas-DD is collecting the full size-range of depositing particles and most importantly the larger particles that dominate the dry particle deposition component (Holsen et al., 1992).

Figure 4:
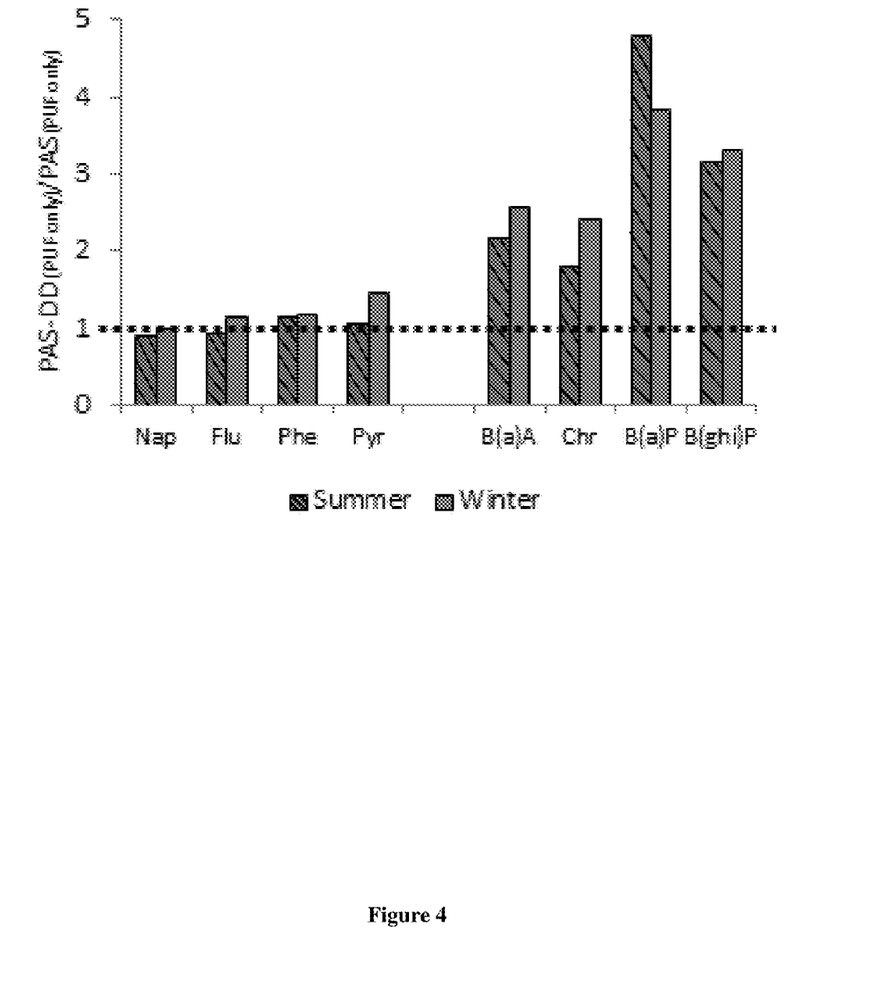
FIG. 4 shows the enhanced ratios ($Pas\text{-}DD_{PUF\ only}/PAS_{PUF\ only}$) for gas-phase (left) and particle-phase (right) PAHs during summer and winter deployments.

The ability of the Pas-DD to capture the dry particle-deposition component of the deposition flux is further illustrated in FIG. 4 which shows enhancement ratios of the Pas-DD versus PAS—when only the PUF is used as the collection substrate. For mainly gas-phase PAHs such as naphthalene, fluorene, phenanthrene and pyrene, there is negligible difference between the results for the two samplers with ratios near 1 for both summer and winter deployments. Both samplers are collecting dry gaseous deposition at similar rates. Based on the recent field calibration of the PUF disk passive air sampler for PAHs (Harner et al., 2013), this sampling rate is equivalent to about 5 m3/day which can be converted to a deposition velocity of about 0.16 cm/s for gas phase PAHs based on the full PUF disk surface area of 365 cm$^2$. This is in the range of deposition velocities reported by Chang et al. (2003) for low to medium molecular weight PAHs (0.01 to 0.29 cm/s respectively). However, it is important to note that for the most volatile PAHs (e.g. naphthalene, fluorene), the PUF disk has a limited sorptive capacity and will eventually approach equilibrium (e.g. less than 1 week for naphthalene, ~3 weeks for fluorene). The process for accounting for reduced accumulation as equilibrium is approached in PUF disks is discussed in Harner et al., (2013). In the real environment, the lower molecular weight PAHs are likely equilibrating with surface compartments (e.g. vegetation, soil) (Simonich and Hites, 1994;

Wagrowski and Hites, 1997) so their equilibration in the PUF disks used in the Pas-DD would be analogous.

The enhancement ratios (FIG. 4) for the Pas-DD increase above unity for the higher molecular weight PAHs benzo(a)anthracene, chrysene, benzo(a)pyrene and benzo(g,h,i)perylene which are increasingly associated with atmospheric particles ((Su et al., 2006; Galarneau et al., 2006; Yamasaki et al., 1982; ref; ref). Ratios as high as 3.5 to 5 are observed for PAHs that are entirely particle bound (i.e. benzo(a)pyrene and benzo(g,h,i)perylene). Results for other PAHs are summarized in Table 5 and show a similar behaviour. The enhancement ratios for the high molecular weight PAHs that are totally particle-bound can be translated to deposition velocities associated with dry deposition and are in the range of 0.56 to 0.8 cm/s (i.e. 3.5 to 5 times greater than the 0.16 cm/s estimate for dry gaseous deposition). This finding is consistent with other reports of PAH deposition velocities (Chang et al., 2003; Tasdemir and Esen 2007; Bozlaker et al., 2007; Sheu et al., 1996).

TABLE 5

Enrichment factors (Pas-DD(PUF only)/PAS(PUF only)) for the summer and winter campaign. Note: Anthracene not detected during summer campaign for both the Pas-DD and PAS and retene not reported during winter campaign due to analytical interferences.

| | Summer | Winter |
|---|---|---|
| Naphthalene | 0.89 | 0.99 |
| Acenaphthylene | 1.11 | 3.14 |
| Acenaphthene | 0.99 | 0.96 |
| Fluorene | 0.91 | 1.15 |
| Phenanthrene | 1.13 | 1.16 |
| Anthracene | n/a | 1.61 |
| Retene | 0.93 | n/a |
| Fluoranthene | 1.22 | 1.35 |
| Pyrene | 1.04 | 1.44 |
| Dibenzothiophene | 1.03 | 0.86 |
| Benzo(a)anthracene | 2.17 | 2.56 |
| Chrysene | 1.8 | 2.41 |
| Benzo(b)fluoranthene | 3.26 | 2.99 |
| Benzo(k)fluoranthene | 2.96 | 3.25 |
| Benzo(a)pyrene | 4.79 | 3.82 |
| Perylene | 3.16 | 3.93 |
| Indeno(123-cd)pyrene | 2.49 | 3.56 |
| Dibenz(ah)anthracene | 8.44 | 3.33 |
| Benzo(ghi)perylene | 3.16 | 3.3 |

One or more currently preferred embodiments have been described by way of example. It will be apparent to persons skilled in the art that a number of variations and modifications can be made without departing from the scope of the disclosure as defined in the claims.

REFERENCES

Bargagli, R.; Brown, D. H.; Nelli, L. Metal biomonitoring with mosses: procedures for correcting for soil contamination. Environ. Pollut. 1995, 89(2), 169-175.

Bartkow, M. E.; Kennedy, K. E.; Huckins, J. N.; Holling, N.; Komarova, T.; Müller, J. F. Photodegradation of polyaromatic hydrocarbons in passive air samplers: Field testing different deployment chambers. Environ. Pollut. 2006, 144(2), 371-376.

Bidleman, T. F.; Billings, W. N.; Foreman, W. T. Vapor-particle partitioning of semivolatile organic compounds: estimates from field collections. Environ. Sci. Technol. 1986, 20(10), 1038-1043.

Bozlaker, A.; Muezzinoglu, A.; Odabasi, M. Atmospheric concentrations, dry deposition and air-soil exchange of polycyclic aromatic hydrocarbons (PAHs) in an industrial region in Turkey. J. Hazard. Mater. 2008, 153(3), 1093-1102.

Chaemfa, C.; Wild, E.; Davison, B.; Barber, J. L.; Jones, K. C. A study of aerosol entrapment and the influence of wind speed, chamber design and foam density on polyurethane foam passive air samplers used for persistent organic pollutants. J. Environ. Monit. 2009, 11(6), 1135-1139.

Chang, K. F.; Fang, G. C.; Lu, C.; Bai, H. Estimating PAH dry deposition by measuring gas and particle phase concentrations in ambient air. Aerosol Air Qual. Res. 2003, 3, 41-51.

Davidson, C. I.; Lindberg, S. E.; Schmidt, J. A.; Cartwright, L. G.; Landis, L. R. Dry deposition of sulfate onto surrogate surfaces. J. Geophys. Res., [Atmos.]. 1985, 90(D1), 2123-2130.

Esen, F.; Siddik Cindoruk, S.; & Tasdemir, Y. Bulk deposition of polycyclic aromatic hydrocarbons (PAHs) in an industrial site of Turkey. Environ. Pollut. 2008, 152(2), 461-467.

Galarneau, E.; Bidleman, T. F.; Blanchard, P. Seasonality and interspecies differences in particle/gas partitioning of PAHs observed by the Integrated Atmospheric Deposition Network (IADN). Atmos. Environ. 2006, 40(1), 182-197.

Hageman, K. J.; Hafner, W. D.; Campbell, D. H.; Jaffe, D. A.; Landers, D. H.; Simonich, S. L. M. Variability in pesticide deposition and source contributions to snowpack in western US national parks. Environ. Sci. Technol. 2010, 44(12), 4452-4458.

Halsall, C. J.; Coleman, P. J.; Jones, K. C. Atmospheric deposition of polychlorinated dibenzo-p-dioxins/dibenzofurans (PCDD/Fs) and polycyclic aromatic hydrocarbons (PAHs) in two UK cities. Chemosphere. 2008, 35(9), 1919-1931.

Harner, T.; Su, K.; Genualdi, S.; Karpowicz, J.; Ahrens, L.; Mihele, C.; Schuster, J.; Charland, J.; Narayan, J. Calibration and Application of PUF Disk Passive Air Samplers for Tracking Polycyclic Aromatic Compounds (PAHs). Atmos. Environ. 2013, 75, 123-128.

Holsen, T. M.; Noll, K. E. Dry deposition of atmospheric particles: application of current models to ambient data. Environ. Sci. Technol. 1992, 26(9), 1807-1815.

IADN (Integrated Atmospheric Deposition Network). 2006, http://www.msc.ec.gc.ca/iadn/

Jaward, F. M.; Farrar, N. J.; Harner, T.; Sweetman, A. J.; Jones, K. C. Passive air sampling of polycyclic aromatic hydrocarbons and polychlorinated naphthalenes across Europe. Environ. Toxicol. Chem. 2004, 23(6), 1355-1364.

Kelly, E. N.; Short, J. W.; Schindler, D. W.; Hodson, P. V.; Ma, M.; Kwan, A. K.; Fortin, B. L. Oil sands development contributes polycyclic aromatic compounds to the Athabasca River and its tributaries. Proc. Natl. Acad. Sci. U.S.A. 2009, 106(52), 22346-22351.

Klánová, J.; Èupr, P.; Kohoutek, J.; Harner, T. Assessing the influence of meteorological parameters on the performance of polyurethane foam-based passive air samplers. Environ. Sci. Technol. 2007, 42(2), 550-555.

Odabasi, M.; Sofuoglu, A.; Vardar, N.; Tasdemir, Y.; Holsen, T. M. Measurement of dry deposition and air-water exchange of polycyclic aromatic hydrocarbons with the water surface sampler. Environ. Sci. Technol. 1999, 33(3), 426-434.

Seaward, M. R. D.; Heslop, J. A.; Green, D.; Bylińska, E. A. Recent levels of radionuclides in lichens from southwest Poland with particular reference to 134Cs and 137Cs. J. Environ. Radioact. 1988, 7(2), 123-129.

Sheu, H. L.; Lee, W. J.; Su, C. C.; Chao, H. R.; Fan, Y. C. Dry deposition of polycyclic aromatic hydrocarbons in ambient air. J. Environ. Eng. (Reston, Va., U.S.). 1996, 122(12), 1101-1109.

Shoeib, M.; Harner, T. Characterization and comparison of three passive air samplers for persistent organic pollutants. Environ. Sci. Technol. 2002, 36(19), 4142-4151.

Simonich, S. L.; & Hites, R. A. Vegetation-atmosphere partitioning of polycyclic aromatic hydrocarbons. Environ. Sci. Technol. 1994, 28(5), 939-943.

Steinnes, E. A critical evaluation of the use of naturally growing moss to monitor the deposition of atmospheric metals. Sci. Total Environ. 1995, 160, 243-249.

Su, Y.; Lei, Y. D.; Wania, F.; Shoeib, M.; Harner, T. Regressing gas/particle partitioning data for polycyclic aromatic hydrocarbons. Environ. Sci. Technol. 2006, 40(11), 3558-3564.

Su, Y.; Wania, F.; Harner, T.; Lei, Y. D. Deposition of polybrominated diphenyl ethers, polychlorinated biphenyls, and polycyclic aromatic hydrocarbons to a boreal deciduous forest. Environ. Sci. Technol. 2007, 41(2), 534-540.

Tasdemir, Y.; Esen, F. Dry deposition fluxes and deposition velocities of PAHs at an urban site in Turkey. Atmos. Environ. 2007, 41(6), 1288-1301.

Thomas, J.; Holsen, T. M.; Dhaniyala, S. Computational fluid dynamic modeling of two passive samplers. Environ. Pollut. 2006, 144(2), 384-392.

Tuduri, L.; Harner, T.; Hung, H. Polyurethane foam (PUF) disks passive air samplers: Wind effect on sampling rates. Environ. Pollut. 2006, 144(2), 377-383.

Wagrowski, D. M.; Hites, R. A. Polycyclic aromatic hydrocarbon accumulation in urban, suburban, and rural vegetation. Environ. Sci. Technol. 1996, 31(1), 279-282.

Wolterbeek, B. Biomonitoring of trace element air pollution: principles, possibilities and perspectives. Environ. Pollut. 2002, 120(1), 11-21.

Yamasaki, H.; Kuwata, K.; Miyamoto, H. Effects of ambient temperature on aspects of airborne polycyclic aromatic hydrocarbons. Environ. Sci. Technol. 1982, 16(4), 189-194.

Zhang, L.; Gong, S.; Padro, J.; Barrie, L. A size-segregated particle dry deposition scheme for an atmospheric aerosol module. Atmos. Environ. 2001, 35(3), 549-560.

What is claimed is:

1. A passive air sampling device, comprising:
   a top cover plate;
   a bottom plate connected to and spaced a distance apart from the top cover plate; and
   at least one sampling media supported by the bottom plate and positioned within the device in an orientation accessible for collecting particles in the environment, wherein the top cover plate and the bottom plate are connected by one or more vertical spacers.

2. The device according to claim 1, wherein the vertical spacers are height adjustable to facilitate adjustment of the distance between the top cover plate, the at least one sampling media and/or the bottom plate.

3. The device according to claim 1, wherein the bottom plate comprises at least one perforation or opening to increase accessibility of the sampling media to particles in the environment.

4. The device according to claim 1, further comprising a support ring connected to and positioned between the top cover plate and the bottom plate.

5. The device according to claim 4, wherein the support ring is substantially parallel to the top cover plate and the bottom plate and provides additional support to the sampling media.

6. The device according to claim 5, wherein the sampling media is supported between the bottom plate and the support ring.

7. The device according to claim 4, wherein at least one of the top cover plate, the support ring, the sampling media, and the bottom plate are shaped to allow for multidirectional air sampling.

8. The device according to claim 7, wherein the top cover plate, the support ring, the sampling media, and the bottom plate are rounded or circular in shape.

9. The device according to claim 8, wherein the top cover plate is dimensioned with a larger diameter than the sampling media, effective to cover the sampling media while maintaining accessibility of the sampling media for collecting particles in the environment.

10. The device according to claim 9, wherein the diameter of the top cover plate is larger than the diameter of the support ring, the sampling media, and the bottom plate.

11. The device according to claim 1, further comprising a bracket for mounting the device to a support structure.

12. The device according to claim 1, wherein the sampling media is spaced apart from the top cover plate a distance ranging from about 0.1 cm to about 7 cm.

13. The device according to claim 1, wherein the sampling media is spaced apart from the top cover plate a distance ranging from about 1 cm to about 3 cm.

14. The device according to claim 1, wherein the sampling media is spaced apart from the top cover plate a distance which is about 2 cm.

15. The device according to claim 1, wherein the sampling media comprises media suitable for sampling volatile, semi-volatile, or particulate matter in air, or combinations thereof.

16. The device according to claim 1, wherein the sampling media comprises a porous sampling media.

17. The device according to claim 1, wherein the sampling media comprises a polyurethane foam (PUF) and/or and other polymer matrices.

18. The device according to claim 1, wherein the sampling media comprises a glass fiber filter.

19. The device according to claim 1, wherein the bottom plate comprises a beveled edge.

20. The device of claim 1, wherein the device is adapted for monitoring air deposition of volatile, semi-volatile, or particulate matter in a region.

21. The device of claim 1, wherein the device is adapted for monitoring organic or inorganic air toxins or contaminants.

22. The device of claim 1, wherein the device is adapted for monitoring air deposition of polycyclic aromatic hydrocarbons.

23. A method of sampling air for volatile, semi-volatile, or particulate matter in a region, said method comprising:
   providing at least one passive air sampling device comprising:
      a top cover plate;
      a bottom plate connected to and spaced a distance apart from the top cover plate; and
      at least one sampling media supported by the bottom plate and positioned within the device in an orientation accessible for collecting particles in the environment, wherein the top cover plate and the bottom plate are connected by one or more vertical spacers;

positioning said at least one passive air sampling device in said region and allowing any volatile, semi-volatile, or particulate matter in the air to deposit on the sampling media of said device over a period of time; and collecting the sampling media from said at least one passive air sampling device at the end of the air sampling period.

24. The method of claim 23, further comprising steps of analyzing the sampling media collected from the at least one passive air sampling device, and determining concentrations of volatile, semi-volatile, and/or particulate matter in the sampled air based on quantities of volatile, semi-volatile, or particulate matter deposited on said sampling media.

* * * * *